US00PP30708P3

(12) United States Plant Patent
Wood

(10) Patent No.: US PP30,708 P3
(45) Date of Patent: Jul. 16, 2019

(54) ***CHAMAECYPARIS* PLANT NAMED 'SMNCLGTB'**

(50) Latin Name: *Chamaecyparis lawsoniana*
Varietal Denomination: SMNCLGTB

(71) Applicant: Timothy Wood, Spring Lake, MI (US)

(72) Inventor: Timothy Wood, Spring Lake, MI (US)

(73) Assignee: Spring Meadow Nursery, Inc., Grand Haven, MI (US)

( * ) Notice: Subject to any disclaimer, the term of this patent is extended or adjusted under 35 U.S.C. 154(b) by 0 days.

(21) Appl. No.: 15/732,452

(22) Filed: Nov. 14, 2017

(65) Prior Publication Data

US 2019/0150340 P1 May 16, 2019

(51) Int. Cl.
*A01H 7/00* (2006.01)

(52) U.S. Cl.
USPC ..... Plt./213

(58) Field of Classification Search
USPC ..... Plt./213
CPC ... A01H 7/00; A01H 5/04; A01H 6/00; A01H 5/00; A01H 5/02; A01H 5/025
See application file for complete search history.

(56) References Cited

PUBLICATIONS

Spring Meadow Nursery Flowering Shrubs Starter Plants Catalog and Shrub Reference 2017-2018, retrieved on Oct. 11, 2018, retrieved from the Internet at https://springmeadownursery.com/files/resource_files/2017-18_SMN_Catalog_1-50.pdf, pp. 1-9 and 37. (Year: 2017).*

* cited by examiner

*Primary Examiner* — June Hwu
(74) *Attorney, Agent, or Firm* — Cassandra Bright

(57) ABSTRACT

A new and distinct *Chamaecyparis* cultivar named 'SMNCLGTB' is disclosed, characterized by colorful foliage, having green and gold coloration. Foliage is distinctively soft and not prickly. Plants are low maintenance with a narrow form. The new cultivar is a *Chamaecyparis*, suitable for ornamental garden purposes.

2 Drawing Sheets

Latin name of the genus and species: *Chamaecyparis lawsoniana.*

Variety denomination: 'SMNCLGTB'.

BACKGROUND OF THE INVENTION

The new cultivar is a product of chance discovery by the inventor, Timothy Wood. This new variety, hereinafter referred to as 'SMNCLGTB', was selected as a naturally occurring branch mutation from an unnamed, unpatented *Chamaecyparis lawsoniana*. The novel variety was discovered in a poly-greenhouse in Grand Haven, Mich. during 2006.

After identifying the new variety as a potentially interesting selection, first propagation of 'SMNCLGTB' occurred by softwood cuttings at a commercial nursery in Grand Haven, Mich. in 2010. The inventor continued controlled testing and propagation, assessing stability of the unique characteristics of this variety. Five generations have been reproduced and have shown that the unique features of this cultivar are stable and reproduced true to type.

SUMMARY OF THE INVENTION

The cultivar 'SMNCLGTB' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'SMNCLGTB' These characteristics in combination distinguish 'SMNCLGTB' as a new and distinct *Chamaecyparis* cultivar:

1. Very colorful foliage with green and gold.
2. Soft texture.
3. Narrow plant form.
4. Low maintenance.

PARENT COMPARISON

'SMNCLGTB' is similar in most horticultural characteristics to the parent, however, plants of 'SMNCLGTB' differ in the following:

1. New cultivar has a softer texture; parent foliage is more prickly.
2. The new cultivar has foliage with gold tips, the parent variety does not have this distinctive coloration.

COMMERCIAL COMPARISON

'SMNCLGTB' can be compared to the commercial variety *Chamaecyparis lawsoniana* 'MINLEM', U.S. Plant Pat. No. 22,359. The varieties are similar in most horticultural characteristics, however, plants of 'SMNCLGTB' differ in the following ways:

3. New cultivar has a softer texture; comparator foliage is more prickly.
4. New cultivar plant shape is more narrow than plants of this comparator.
5. New cultivar's gold tips are more distinct; comparator has less distinct color change within leaves.

BRIEF DESCRIPTION OF THE PHOTOGRAPHS

Figure 1:
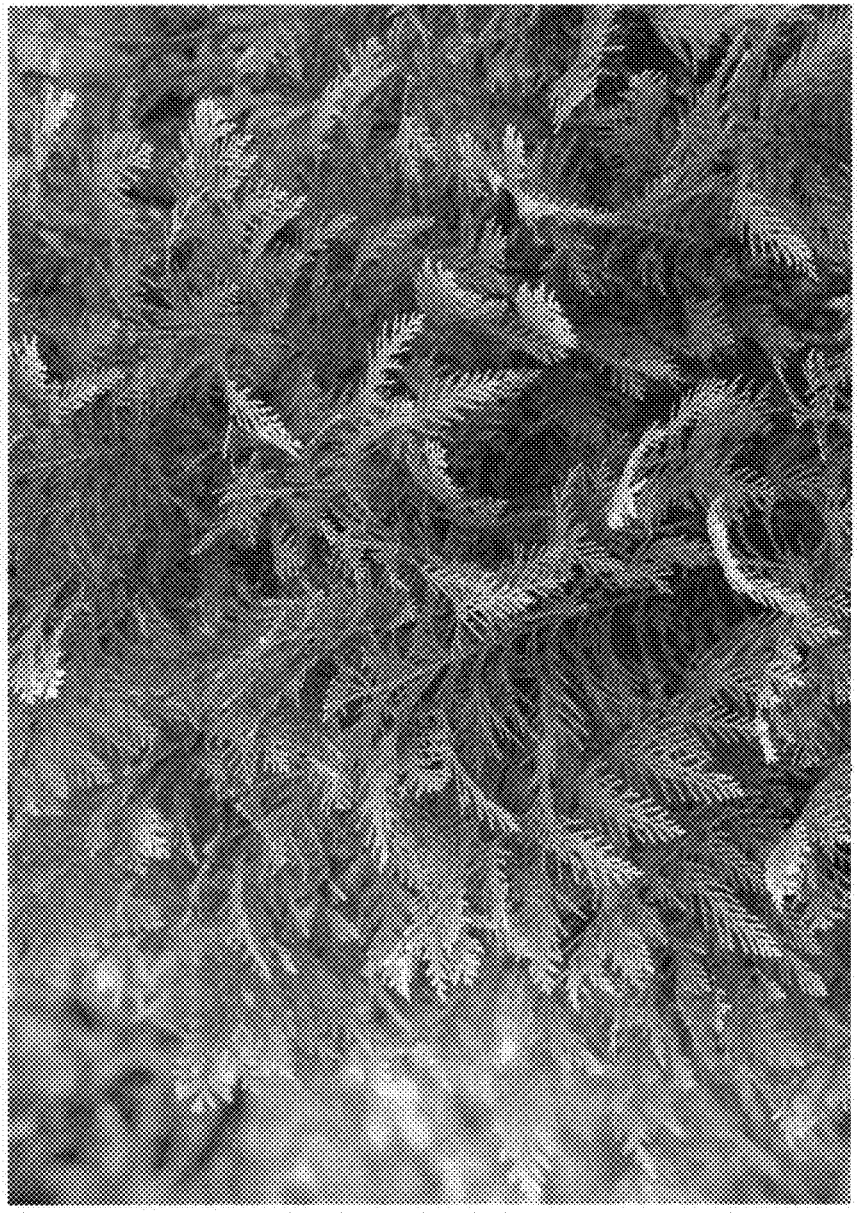

The accompanying photograph in FIG. 1 illustrates in full color typical foliage of 'SMNCLGTB' on a mature plant of approximately 5 years old, grown outdoors in Grand Haven, Mich.

Figure 2:
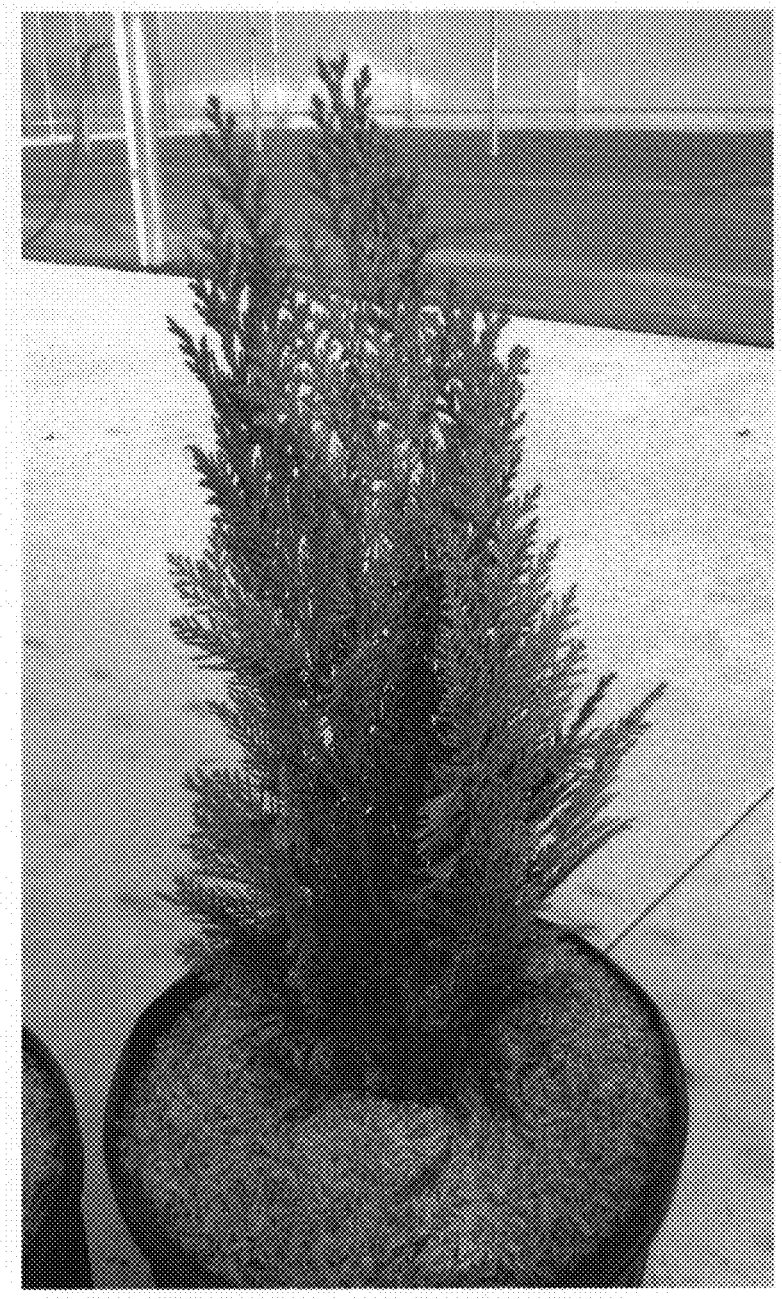

FIG. 2 illustrates a plant of the new variety at approximately 1.5 years old in a 3 gallon container.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015 except where general terms of ordinary dictionary significance are used. The following observations and measurements describe 'SMNCLGTB' plants grown in a poly greenhouse during Summer, in Grand Haven, Mich. USA. The growing temperature ranged from 18° C. to 27° C. during the day and from 5° C. to 10° C. during the night. General light conditions are natural sunlight. Measurements and numerical values represent averages of typical plant types.

Botanical classification: *Chamaecyparis lawsoniana* 'SMNCLGTB'.

PROPAGATION

Typical method: Softwood cuttings.
Time to initiate rooting: 120 days at approximately 10° C.
Time to produce a rooted young plant: 180 days at approximately 10° C. to 13° C.
Root description: Fine and fleshy roots present. Moderately well branched. Colored light brown, not accurately measured with an R.H.S. chart.

PLANT

Age of plant described: 2 years.
Container size of plant described: 3 gallon.
Growth habit: Upright, semi-narrow evergreen tree.
Height: 30 cm in a 1 gallon container.
Plant spread: 17 cm in a 1 gallon container.
Typical growth rate: Moderate.
Pinching required: Preferred to encourage branching, not required.
Branching characteristics: Upwards, columnar.
Angle: About 45° from main leader.
Quantity of lateral branches: 21.
Length of lateral branches: 8-14 cm.
Diameter of lateral branches: 3 mm.
Lateral branch shape: Round with overlapping scales.
Stem strength: Very strong.
Stem color:
*Young*.—Green 141B.
*Older*.—Greyed-Brown 199A.
Internode length: 1 cm.
Branch orientation:
*Immature*.—Average range 15 to 45 degrees from center.
*Mature*.—Average range 15 to 45 degrees from center.
Trunk bark:
*Color*.—Near RHS Grey-Brown N199A.
*Texture*.—Rough, moderately scaly.

FOLIAGE

General description: Overlapping scales. Smooth, soft texture.
Leaf:
*Arrangement*.—Alternate overlapping scales.
*Shape of blade*.—Scale-like.
*Average length*.—2 mm.
*Average width*.—1 mm.
*Apex*.—Apiculate.
*Base*.—Cuneate.
*Margin*.—Entire.
*Texture of top surface*.—Smooth, not prickly.
*Texture of bottom surface*.—Smooth, not prickly.
*Foliage color*.—Young, upper side: Green N138B with overlay of Blue-Green 122D. Tips of leaves: Yellow-Green N144A. Young, under side: Green N138B with overlay of Blue-Green 122D. Tips of leaves: Yellow-Green N144A. Mature, upper side: Green N138B with overlay of Blue-Green 122D. Tips of leaves: Yellow-Green N144A. Mature, under side: Green N138B with overlay of Blue-Green 122D. Tips of leaves: Yellow-Green N144A.
*Venation*.—Not observable.
*Fragrance*.—Not observed.

FLOWER

Flowering not observed.

OTHER CHARACTERISTICS

Disease and pest resistance: Neither resistance nor susceptibility observed.
Drought tolerance: No tolerance for drought.
Temperature tolerance: −29 to 36 degree C.

What is claimed is:

1. A new and distinct cultivar of *Chamaecyparis* plant named 'SMNCLGTB' as herein illustrated and described.

* * * * *